US012251435B2

United States Patent
Li et al.

(10) Patent No.: US 12,251,435 B2
(45) Date of Patent: Mar. 18, 2025

(54) ENGINEERED HANSENULA FUNGI EFFICIENTLY EXPRESSING CA10 VIRUS-LIKE PARTICLES AND USES THEREOF

(71) Applicant: Beijing Minhai Biotechnology Co., Ltd., Beijing (CN)

(72) Inventors: Guoshun Li, Beijing (CN); Meirong Gu, Beijing (CN); Lin Guo, Beijing (CN); Wei Jian, Beijing (CN); Junjie Liu, Beijing (CN); Haifeng Xiao, Beijing (CN); Gaimei Zhang, Beijing (CN); Lili Zhao, Beijing (CN); Xuechao Xie, Beijing (CN); Lei Chen, Beijing (CN); Yingzhi Xu, Beijing (CN); Jiankai Liu, Beijing (CN)

(73) Assignee: Beijing Minhai Biotechnology Co., Ltd., Beijing (CN)

( * ) Notice: Subject to any disclaimer, the term of this patent is extended or adjusted under 35 U.S.C. 154(b) by 796 days.

(21) Appl. No.: 17/299,520

(22) PCT Filed: Sep. 3, 2020

(86) PCT No.: PCT/CN2020/113181
§ 371 (c)(1),
(2) Date: Jun. 3, 2021

(87) PCT Pub. No.: WO2021/253645
PCT Pub. Date: Dec. 23, 2021

(65) Prior Publication Data
US 2022/0118075 A1 Apr. 21, 2022

(30) Foreign Application Priority Data
Jun. 19, 2020 (CN) .......................... 202010566780.1

(51) Int. Cl.
| | | |
|---|---|---|
| *A61K 39/135* | (2006.01) | |
| *A61K 39/00* | (2006.01) | |
| *A61P 31/14* | (2006.01) | |
| *C07K 14/09* | (2006.01) | |
| *C12N 7/00* | (2006.01) | |
| *C12N 15/81* | (2006.01) | |

(52) U.S. Cl.
CPC ............ *A61K 39/135* (2013.01); *A61P 31/14* (2018.01); *C07K 14/09* (2013.01); *C12N 7/00* (2013.01); *C12N 15/815* (2013.01); *A61K 2039/5258* (2013.01); *A61K 2039/55505* (2013.01)

(58) Field of Classification Search
CPC .......... A61K 39/135; A61K 2039/5258; A61K 2039/55505; A61P 31/14; C07K 14/09; C12N 7/00; C12N 15/815
See application file for complete search history.

(56) References Cited

U.S. PATENT DOCUMENTS

| | | | | |
|---|---|---|---|---|
| 9,782,471 | B2 * | 10/2017 | Gu | ........................ A61K 39/125 |
| 10,987,416 | B2 * | 4/2021 | Li | ........................ A61K 39/125 |
| 2017/0056491 | A1 | 3/2017 | Chow et al. | |

FOREIGN PATENT DOCUMENTS

| | | | | |
|---|---|---|---|---|
| CN | 103045492 | | 4/2013 | |
| CN | 107384944 | | 11/2017 | |
| CN | 108624601 | | 10/2018 | |
| CN | 109384832 | | 2/2019 | |
| CN | 108624601 B | * | 8/2023 | ............. A61K 39/12 |

OTHER PUBLICATIONS

Gu et al. 2018. GenBank Accession No. MI104398.1. SEQ ID No. 3 from U.S. Pat. No. 9,782,471 B2 (Year: 2018).*
Guo, W. P. et al. (2015). Fourteen types of co-circulating recombinant enterovirus were associated with hand, foot, and mouth disease in children from Wenzhou, China. Journal of clinical virology : the official publication of the Pan American Society for Clinical Virology, 70, 29-38. (Year: 2015).*
Guo et al. GenBank Accession No. ALB72971.1. Direct Submission. Submitted Nov. 21, 2014 (Year: 2014).*
Gu et al. CN 103045492 A. Machine translation to English. (Year: 2013).*
Chen, M., He, S., Yan, Q., Xu, X., Wu, W., Ge, S., Zhang, S., Chen, M., & Xia, N. (2017). Severe hand, foot and mouth disease associated with Coxsackievirus A10 infections in Xiamen, China in 2015. Journal of Clinical Virology, 93, 20-24. (Year: 2017).*
Xu, M., Su, L., Cao, L., Zhong, H., Dong, N., Dong, Z., Xu, J., & Zhang, C. (2015). Genotypes of the Enterovirus Causing Hand Foot and Mouth Disease in Shanghai, China, 2012-2013. PloS One, 10(9), e0138514-e0138514. (Year: 2015).*
Xu, M., Su, L., Cao, L., Zhong, H., Dong, N., & Xu, J. (2013). Enterovirus genotypes causing hand foot and mouth disease in Shanghai, China: a molecular epidemiological analysis. BMC Infectious Diseases, 13(1), 489-489. (Year: 2013).*
Gellissen, G. et al. (2005). New yeast expression platforms based on methylotrophic Hansenula polymorpha and Pichia pastoris and on dimorphic Arxula adeninivorans and Yarrowia lipolytica—A comparison. FEMS Yeast Research, 5(11), 1079-1096. (Year: 2005).*
Huang et al. (2023). CN 108624601 B. Machine translation (Year: 2023).*
Zhang et al., "Characterization of an inactivated whole-virus bivalent vaccine that induces balanced protective immunity against coxsackievirus A6 and A10 in mice" Vaccine, 2018, 36(46), pp. 7095-7104.

(Continued)

*Primary Examiner* — Rachel B Gill
*Assistant Examiner* — Carey Alexander Stuart
(74) *Attorney, Agent, or Firm* — Westbridge IP LLC (57) ABSTRACT

The present disclosure provides an engineered *Hansenula* fungus that efficiently expresses CA10 (Coxsackievirus A10) virus-like particles and uses thereof. The engineered fungus includes a recombinant vector carrying the P1 and 3CD genes of the CA10 virus optimized according to preferred codons of *Hansenula*. The present disclosure also provides a preparation method for CA10 virus-like particles and vaccines prepared therefrom.

5 Claims, 3 Drawing Sheets
Specification includes a Sequence Listing.

(56) References Cited

OTHER PUBLICATIONS

Zhou et al., "A virus-like particle vaccine protects mice against coxsackievirus A10 lethal infection", Antiviral Research, 2018, 152, pp. 124-130.

* cited by examiner

SEQUENCE LISTING

```
<160> NUMBER OF SEQ ID NOS: 2

<210> SEQ ID NO 1
<211> LENGTH: 2592
<212> TYPE: DNA
<213> ORGANISM: Artificial Sequence
<220> FEATURE:
<223> OTHER INFORMATION: Laboratory synthesis

<400> SEQUENCE: 1
atgggtgccc aggtgtctac ccagaagtct ggttctcacg agaccggtaa cgtggccacc      60
ggtggttcta ccatcaactt caccaacatc aactactaca aggactctta cgccgcctct     120
gccaccagac aggacttcac ccaggaccca aagaagttca cccagccagt gctggactct     180
atcagagagc tgtctgcccc actgaactct ccatctgtgg aggcctgcgg ttactctgac     240
agagtggccc agctgaccgt gggtaactct tctatcacca cccaggaggc cgccaacatc     300
```

-continued

```
gtgctggcct acggtgagtg gccagagtac tgcccagaca ccgacgccac cgccgtggac    360
aagccaacca gaccagacgt gtctgtgaac agattctaca ccctggactc taagatgtgg    420
caggagaact ctaccggttg gtactggaag ttcccagacg tgctgaacaa gaccggtgtg    480
ttcggtcaga acgccagtt ccactacctg tacagatccg gtttctgcct gcacgtgcag    540
tgcaacgcct ctaagttcca ccagggtgcc ctgctggtgg ccgtgatccc agagttcgtg    600
atcgccggta gaggttctaa caccaagcca acgaggccc acacccagg tttcaccacc    660
accttcccag gtaccaccgg tgccaccttc cacgacccat acgtgctgga ctctggtgtg    720
ccactgtctc aggccctgat ctacccacac cagtggatca acctgagaac caacaactgc    780
gccaccgtga tcgtgccata catcaacgcc gtgccattcg actctgccat caaccactct    840
aacttcggtc tgatcgtgat cccagtgtct ccactgaagt actcttctgg tgccaccacc    900
gccatcccaa tcaccatcac catcgcccca ctgaactctg agttcggtgg tctgagacag    960
gccgtgtctc agggtatccc agccgagctg agaccaggta ccaaccagtt cctgaccacc   1020
gacgacgaca ccgccgcccc aatcctgcca ggtttcaccc caaccccaac catccacatc   1080
ccaggtgagg tgcactctct gctggagctg tgcagagtgg agaccatcct ggaggtgaac   1140
aacaccaccg aggccaccgg tctgaccaga ctgctgatcc cagtgtcttc tcagaacaag   1200
gccgacgagc tgtgcgccgc cttcatggtg gacccaggta gaatcggtcc atggcagtct   1260
accctggtgg gtcagatttg cagatactac acccagtggt tggttctct gaaggtgacc   1320
ttcatgttca ccggttcttt catggccacc ggtaagatgc tggtggccta ctctccacca   1380
ggttctgccc agccagccaa cagagagacc gccatgctgg gtacccacgt gatctgggac   1440
ttcggtctgc agtcttctgt gtctctggtg atcccatgga tctctaacac ccacttcaga   1500
accgccaaga ccggtggtaa ctacgactac tacaccgccg gtgtggtgac cctgtggtac   1560
cagaccaact acgtggtgcc accagagacc ccaggtgagg cctacatcat cgccatgggt   1620
gccgccagg acaacttcac cctgaagatt tgcaaggaca ccgacgaggt gacccagcag   1680
gccgtgctgc agggtgaccc agtggaggac atcatccacg acgccctggg taacaccgcc   1740
agaagagcca tctcttctgc caccaacgtg gagtctgccg ccaacaccac cccatcttct   1800
cacagactgg agaccggtag agtgccagcc ctgcaggccg ccgagaccgg tgccacctct   1860
aacgccaccg acgagaacat gatcgagacc agatgcgtgg tgaacagaaa cggtgtgctg   1920
gagaccacca tcaaccactt cttctctaga tccggtctgg tgggtgtggt gaacctgacc   1980
gacggtggta ccgacaccac cggttacgcc acctgggaca tcgacatcat gggtttcgtg   2040
cagctgagaa gaaagtgcga gatgttcacc tacatgagat caacgccga gttcaccttc   2100
gtgaccacca ccgagaacgg tgaggccaga ccatacatgc tgcagtacat gtacgtgcca   2160
ccaggtgccc caaagccaac cggtagagac gccttccagt ggcagaccgc caccaaccca   2220
tctgtgttcg tgaagctgac cgacccacca gccaggtgt ctgtgccatt catgtctcca   2280
gcctctgcct accagtggtt ctacgacggt tacccaacct tcggtcagca cccagagacc   2340
tctaacacca cctacggtct gtgcccaaac aacatgatgg gtaccttcgc cgtgagagtg   2400
gtgtctagag aggcctctca gctgaagctg cagaccagtg tacatgaa gctgaagcac   2460
gtgagagcct gggtgccaag accaatcaga tcccagccat acctgctgaa gaacttccca   2520
aactacgact cttctaagat caccaactct gccagagaca gatcctctat caagcaggcc   2580
aacatgtaat ag                                                       2592
```

<210> SEQ ID NO 2
<211> LENGTH: 1944
<212> TYPE: DNA
<213> ORGANISM: Artificial Sequence
<220> FEATURE:
<223> OTHER INFORMATION: Laboratory synthesis

<400> SEQUENCE: 2

```
atgggtccat ctctggactt cgccctgtct ctgctgagaa gaaacatcag acaggtgcag      60
accgaccagg gtcacttcac catgctgggt gtgagagaca gactggccat cctgccaaga     120
cactctcagc caggtaagac catctggggtg gagcacaagc tggtgaacgt gctggacgcc     180
gtggagctgg tggacgagca gggtgtgaac ctggagctga ccctggtgac cctggacacc     240
aacgagaagt tcagagacgt gaccaagttc atcccagaga acatctctgg tgcctctgac     300
gccaccctgg tgatcaacac cgagcacatg ccatctatgt tcgtgccagt gggtgacgtg     360
gtgcagtacg gtttcctgaa cctgtctggt aagccaaccc acagaaccat gatgtacaac     420
ttcccaacca aggccggtca gtgcggtggt gtggtgacct ctgtgggtaa gatcatcggt     480
atccacatcg gtggtaacgg tagacagggt ttctgcgccg gtctgaagag atcctacttc     540
gcctctgagc agggtgagat ccagtgggtg aagccaaaca aggagaccgg tagactgaac     600
atcaacggtc aaccagaac caagctggag ccatctgtgt ccacgacgt gttcgagggt     660 aacaaggagc agccgtgct gacctctaag gacccaagac tggaggtgga cttcgagcag     720
gccctgttct ctaagtacgt gggtaacgtg ctgcacgagc cagacgagta cgtgaagcag     780
gccgccctgc actacgccaa ccagctgaag cagctggaca tcaacaccaa caagatgtct     840
atggaggagg cctgctacgg taccgagaac ctggaggcca tcgacctgca cacctctgcc     900
ggttacccat actctgccct gggtatcaag aagagagaca tcctggaccc aaccaccaga     960
gacaccacca agatgaagtt ctacatggac aagtacggtc tggacctgcc atactctacc    1020
tacgtgaagg acgagctgag atccctggac aagatcaaga agggtaagtc tagactgatc    1080
gaggcctctt ctctgaacga ctctgtgtac ctgagaatga ccttcggtca cctgtacgag    1140
gccttccacg ccaacccagg taccgtgacc ggttctgccg tgggttgcaa cccagacgtg    1200
ttctggtcta gctgccaat cctgctgcca ggttctctgt tcgccttcga ctactctggt    1260
tacgacgcct ctctgtctcc agtgtggttc agagccctgg agatggtgct gagagacatc    1320
ggttactctg aggaggccgt gtctctgatc gagggtatca ccacaccca ccacgtgtac    1380 agaaacaaga cctactgcgt gctgggtggt atgccatctg ttgctctgg tacctctatc    1440 ttcaactcta tgatcaacaa catcatcatc agaaccctgc tgatcaagac cttcaagggt    1500
atcgacctgg acgagctgaa catggtggcc tacggtgacg acgtgctggc ctcttaccca    1560
ttcccaatcg actgcctgga gctggccaag accggtaagg agtacggtct gaccatgacc    1620
ccagccgaca gtctccatg cttcaacgag gtgacctggg agaacgccac cttcctgaag    1680
agaggtttcc tgccagacca ccagttccca ttcctgatcc acccaaccat gccaatgaag    1740
gagatccacg agtctatcag atggaccaag gacgcctgca cacccagga ccacgtgaga    1800 tccctgtgcc tgctggcctg gcacaacggt aaggacgagt acgagaagtt cgtgtctacc    1860
atcagatccg tgccagtggg taaggccctg gccatcccaa acttcgagaa cctgagaaga    1920
aactggctgg agctgttcta atag                                           1944
```

ENGINEERED HANSENULA FUNGI EFFICIENTLY EXPRESSING CA10 VIRUS-LIKE PARTICLES AND USES THEREOF

CROSS REFERENCE

This application is a national stage filing under 35 U.S.C. § 371 of International Patent Application No. PCT/CN2020/113181, filed Sep. 3, 2020, which claims priority to Chinese application 2020105667801, filed Jun. 19, 2020, each of which is incorporated by reference herein in its entirety.

TECHNICAL FIELD

The present invention relates to the field of biomedicines, specifically, to *Hansenula* engineering fungi efficiently expressing CA10 virus-like particles and use thereof.

BACKGROUND ART

Hand-foot-and-mouth disease (HFMD) is a common infectious disease in children. It is a type C infectious disease caused by a variety of viruses. Coxsackievirus A10 (CA10) is one of the pathogens of hand-foot-and-mouth disease, mainly infecting children of 5 years old or less. Coxsackievirus A10 is one of the main pathogens of hand-foot-and-mouth disease in China in recent years. CA10 can cause herpangina, a small number of patients show symptoms of the nervous system and even have convulsions or complications of cardiopulmonary function.

Since 2008, Coxsackievirus A10 has been continuously prevalent in some parts of China. In 2010, there was an outbreak of hand-foot-and-mouth disease caused by CA10 in France, and then there was an epidemic of hand-foot-and-mouth caused by the dominant strain of CA10 in many places in China. At present, there is no vaccine to prevent CA10. Therefore, the development of a vaccine is of great significance for the prevention of hand-foot-and-mouth disease.

At present, there are no vaccines targeting CA10 on the market at home and abroad, and most vaccines are in preclinical research, mainly focusing on inactivated vaccines and virus-like particle (VLP) vaccines. Inactivated vaccines have the risk of incomplete inactivation or recovery of virulence, and the epitopes of inactivated vaccines are easily destroyed during inactivation. The proportion of hollow and solid virus particles in inactivated vaccines is difficult to control, resulting in problems such as large differences between batches and low batch yield. Therefore, the development of a cheaper, safer, and effective preventive vaccine against CA10 is of great significance for controlling the prevalence of hand-foot-and-mouth disease in infants and young children.

CA10 virus is a single-stranded positive-stranded RNA virus, with a viral genome of approximately 7.4 kb nucleotides. The virus particle has an icosahedral spherical structure and a diameter of about 28 to 32 nm and is three-dimensionally symmetric. The virus particle has no envelope. The viral protein shell consists of 4 polypeptide chains, namely VP1, VP2, VP3 and VP4. These 4 proteins form a subunit, and 60 subunits constitute the capsid protein of the virus. Studies have shown that the capsid protein of the virus can self-assemble into a VLP in the cell. The virus particle does not carry viral nucleic acid, has no potential carcinogenic risk, has good safety, immune characteristics and biological activity, and can be prepared and purified on a large scale.

The VLP vaccine provides a new opportunity for the development of new, safe and effective vaccines. The VLP vaccine is produced by expressing one or more structural proteins of the virus through molecular biology technology. These structural proteins have natural self-assembly ability and can form a spatial configuration and epitope similar to that of natural virus particles but have no viral nucleic acid. The VLP vaccine is highly immunogenic and non-infectious. There is no risk of incomplete inactivation or recovery of virulence. There is a high density of viral antigens on the surface of the VLP vaccine, and conformational epitopes are preserved. The VLP vaccine can be presented to immune cells in the same way as whole-virus vaccines to effectively induce immune protective responses of the body's immune system. It is also superior in this respect to the destruction of some important antigenic determinants that may occur during inactivation. In addition, another advantage is that it can be modified arbitrarily according to the need to better stimulate the body to produce a protective immune response.

The key issue in the development of VLP preventive vaccines is the ability to prepare a large number of VLP samples with high efficiency and high purity. Therefore, the selection of high-efficiency expression systems and the purification process for obtaining high-purity products are crucial.

SUMMARY OF THE INVENTION

The purpose of the present invention is to provide a *Hansenula* engineering fungus that efficiently expresses CA10 virus-like particles and use thereof.

The concept of the present invention is as follows: on the one hand, the present invention uses the *Hansenula polymorpha* expression system to construct and obtain a strain that efficiently expresses CA10 virus-like particles. The *Hansenula polymorpha* expression system has the characteristics of stable genetic properties, simple operation, easy high-density cultivation, high yield of foreign proteins, low production cost, suitability for large-scale industrial production and the like. It also has the advantage of post-translational processing of foreign proteins that the prokaryotic expression systems do not possess, and avoids the disadvantages of other yeast expression strains such as instability, easy loss of plasmids and excessive glycosylation. *Hansenula polymorpha* expression system is a more advanced VLP vaccine expression system superior to *E. coli* and other eukaryotic expression systems.

On the other hand, the present invention can obtain VLP samples with high purity and high yield through a well-designed purification process. The present invention adopts ultrafiltration and three-step chromatography process to purify the VLP vaccine, has simple process operation, strong controllability, high antigen recovery rate, does not use large-scale equipment such as centrifuges, and is easier to realize large scale production.

In order to achieve the purpose of the present invention, in a first aspect, the present invention provides a *Hansenula* engineering fungus that efficiently expresses CA10 virus-like particles, and the engineering fungus comprises a recombinant vector carrying P1 and 3CD genes of the CA10 virus;

wherein, starting vector of the recombinant vector is PMV-05 (see ZL201210592813.5 for the construction method of vector PMV-05); starting strain of the engineering fungus is uracil auxotroph *Hansenula* AU-0501 (see ZL201210592813.5 for the strain, with an accession number of CGMCC No. 7013);

The P1 and 3CD genes of the CA10 virus are sequence-optimized genes according to most preferred codons of *Hansenula*.

The nucleotide sequences of the optimized P1 and 3CD genes of the CA10 virus are represented by SEQ ID NOs: 1 and 2, respectively.

The nucleotide sequences encoding the P1 and 3CD proteins provided by the present invention use most preferred codons of *Hansenula* for sequence optimization. In order to avoid excessively high GC content of the translated mRNA and the influence of the secondary structure of the mRNA on the translation efficiency, the present invention uses sub-preferred codons for corresponding amino acids, provided that the use frequency of the sub-preferred codons is very close to the most-preferred codons, and the amino acid sequence remains unchanged. At the same time, in some special cases, in order to reduce or increase restriction enzyme cutting sites, appropriate adjustments have been made to part of the sequence.

Optionally, the engineering fungus is obtained by subjecting the P1 and 3CD genes of the CA10 virus to double enzyme digestion with EcoRI and BamHI, then respectively constructing with a vector PMV-05 having been double-enzyme digested by EcoRI and BamHI to obtain a PMV-05-P1 recombinant expression vector and a PMV-05-3CD recombinant expression vector, then respectively subjecting the PMV-05-P1 recombinant expression vector and the PMV-05-3CD recombinant expression vector to enzyme digestion with SacI and XhoI, SacI and SalI, constructing to obtain a PMV-05-P1-3CD co-expression vector, and finally constructing by introducing the co-expression vector into *Hansenula* AU-0501.

Preferably, the engineering fungus is *Hansenula polymorpha* CA10-W, which has been deposited in the China General Microbiological Culture Collection Center (CGMCC), address: Institute of Microbiology Chinese Academy of Sciences, No. 1 West Beichen Road, Chaoyang District, Beijing, China, Postcode: 100101, with an accession number: CGMCC No. 19850, and a depositing date: May 20, 2020.

In the second aspect, the present invention provides use of the engineering fungus in the preparation of CA10 virus-like particles by fermentation.

In the third aspect, the present invention provides a method for preparing CA10 virus-like particles, comprising the following steps:

1) culturing the above-mentioned engineering fungi, so as to express CA10 virus P1 protein and 3CD protein in the engineering fungal cells, and self-assemble into immunogenic virus-like particles; and
2) separating and purifying the virus-like particles (VLP protein).

The step 2) adopts ultrafiltration and three-step chromatography to separate and purify the virus-like particles, comprising:
   A. centrifuging to collect the fungi, breaking the fungi, performing ultrafiltration after the target product is clarified, and collecting the ultrafiltrate;
   B. ion exchange chromatography;
   C. hydroxyapatite chromatography; and
   D. molecular sieve chromatography.

Optionally, the method for breaking the fungi in step A comprises: resuspending the engineering fungi using a cell lysis buffer, and breaking the cells for 2 to 4 times under a pressure of 1100 to 1400 bar; the cell lysis buffer comprises 20 to 100 mM of Tris, 1 to 5 mM of EDTA-Na2 (disodium ethylenediaminetetraacetate), 200 to 1000 mM of NaCl, 1 to 5 mM of PMSF (phenylmethylsulfonyl fluoride), 0.01% to 1.0% of Tween-80, with a pH of 7.5 to 8.5.

Preferably, cell breaking of the engineering fungi is performed twice under a pressure of 1300 bar.

Through a large number of experiments, it is found that the broken rate can reach 50% to 70% after breaking the cells in the present invention once under 1300 bar; the broken rate can reach 85% to 95% after breaking twice, and the broken rate can reach 95% to 98% or more after breaking thrice. Considering the time and cost of breaking and the ratio of VLP protein to impure protein after breaking, it is preferable that the broken rate is greater than 85% after breaking twice.

The method for clarifying the target product comprises: filtering the cell-broken liquid through a depth filter at a filtration flow rate of 900 to 1850 ml/min/m², washing the filter membrane package with a washing solution, and collecting the clarified liquid; the washing solution comprises 20 to 100 mM of Tris, 1 to 5 mM of EDTA-Na2, 200 to 1000 mM of NaCl, and 0.01% to 1.0% of Tween-80, with a pH of 7.5 to 8.5; or
   centrifuging the cell-broken liquid at 6000 to 8000 rpm for 40 to 60 min, and collecting the clarified liquid; or
   subjecting the cell-broken liquid to microfiltration through a 0.65 µm membrane package, and collecting the clarified liquid.

Preferably, a depth filter is used to collect the clarified liquid, the washing solution comprises 50 mM of Tris, 2 mM of EDTA-Na2, 250 mM of NaCl, 0.01% of Tween-80, with a pH of 8.0, and the flow rate is 1200 ml/min/m².

Studies have found that the depth filter used for the cell-broken liquid in the present invention has a flow rate of 1200 ml/min/m². If the flow rate is higher than 1200 ml/min/m², the cell debris removal effect is not ideal, and if the flow rate is lower than 1200 ml/min/m², the processing time is prolonged. Therefore, a debris removal effect can be achieved by using a flow rate of 1200 ml/min/m².

The ultrafiltration method comprises: subjecting the collected clarified liquid to ultrafiltration with a 100 to 500 KD membrane package using a buffer of pH 7.0 to 8.5, and collecting the ultrafiltrate; the buffer is an aqueous solution comprising 20 to 100 mM of tris(hydroxymethyl)aminomethane, 150 to 300 mM of NaCl and 0 to 10% by weight of glycerol.

Preferably, the buffer has a pH of 8.0, and comprises 50 mM of tris(hydroxymethyl)aminomethane and 250 mM of NaCl, and the buffer also comprises 5% by mass fraction of glycerol.

Studies have found that when the buffer range of the tris(hydroxymethyl)aminomethane buffer is 7.1 to 8.9, and when the pH is 8.0, the purification recovery rate of the VLP protein is high, and the impure protein removal effect is good. Studies have shown that in a low-content glycerol solution, the protein will form visible aggregate precipitates and is unstable, but a high concentration of glycerol increases the viscosity of the solution and causes increased pressure of the ultrafiltration and chromatography, which is unfavorable to purification. A glycerin aqueous solution of 5% by weight is used by taking a comprehensive consideration.

The step B ion exchange chromatography comprises: performing equilibrium using a buffer of 5 to 10 column volumes, then loading the sample (ultrafiltrate), collecting the eluate having an ultraviolet absorption peak at UV 280 nm, which is a first-step chromatography protein solution; the buffer is an aqueous solution comprising 20 to 100 mM of tris(hydroxymethyl)aminomethane, 150 to 300 mM of NaCl and 0 to 10% by weight of glycerol, and has a pH of 7.5 to 8.5.

Preferably, an aqueous solution comprising 50 mM of tris(hydroxymethyl)aminomethane, 250 mM of NaCl and 5% by weight of glycerol is used to form a buffer with a pH of 8.0 for equilibrium elution.

Further, an anion exchange chromatography column can be used for ion exchange chromatography, with a medium of Capto Q.

The step C hydroxyapatite chromatography comprises: adding 500 mM of PB solution to the first-step chromatography protein solution to have a final concentration of 10 to 120 mM of PB; using an buffer with a pH of 6.8 to 8.5 formed of an aqueous solution comprising 10 to 120 mM of PBS and 0 to 10% by weight of glycerol to perform equilibrium with 5 to 10 column volumes, then loading the sample (the first-step chromatography protein solution), then using an buffer with a pH of 6.8 to 8.5 formed of an aqueous solution comprising 150 to 400 mM of PBS and 0 to 10% by weight of glycerol for elution, and collecting the eluate having an ultraviolet absorption peak at UV 280 nm, which is a second-step chromatography protein solution.

Preferably, a buffer comprising 60 mM PBS and 5% by weight of glycerol is used for equilibrium to remove impure protein, and a buffer comprising 200 mM PBS and 5% by weight of glycerol is used for elution to obtain the eluted protein solution.

Studies have shown that impure proteins cannot be effectively removed by using a low-concentration (less than 10 mM) PB equilibrium solution in the present invention, resulting in increased pressure of the subsequent purification pressure; the use of a high-concentration (greater than 120 mM) PB equilibrium solution allows a large amount of impure proteins to penetrate together with the target protein, thereby reducing the recovery rate of the target protein; and the use of 60 mM PB equilibrium solution can remove impure proteins by 50% or more.

In the present invention, the target protein cannot be effectively eluted by using a low-concentration (less than 150 mM) PB eluent, so that a large amount of the target protein is adsorbed on the chromatographic medium and cannot be recovered, causing loss; and a large amount of impure proteins are eluted together with the target protein by using a high-concentration (greater than 400 mM) PB equilibrium solution, thus reducing the purification effect. Therefore, the recovery rate of the target protein can reach 80% or more by using 200 mM PB. With a low glycerol content, the proteins will form aggregates and become unstable, and a high concentration of glycerol will increase the viscosity of the solution and cause increased pressure of the ultrafiltration and chromatography, which is unfavorable to purification. Therefore, a 5% by weight of glycerol solution is used.

The step D molecular sieve chromatography comprises: loading the second-step chromatography protein solution onto a molecular sieve chromatography column, eluting using a buffer with a pH of 6.8 to 7.4 containing 100 to 300 mM of NaCl, 0.05%0 to 3%0 (w/v) of Tween-80, and 10 to 50 mM of PBS, and collecting the eluate having an ultraviolet absorption peak at UV 280 nm, which is the target protein solution.

Preferably, 20 mM of PBS, 150 mM of NaCl and 0.1%0 (w/v) of Tween-80 are used to prepare a buffer with a pH of 7.2 for elution.

The medium used for molecular sieve chromatography in the step D is Sephacryl S-300HR.

Studies have shown that in the present invention, if the content of Tween-80 is less than 0.05%0, the proteins will form aggregates and become unstable; a high content of Tween-80 will interfere with the detection of the protein content, and meanwhile, a high content of Tween-80 as an injection additive will cause side reactions. Therefore, the lower the content of Tween-80, the better, provided that the process requirements are met.

In a specific embodiment of the present invention, the method for preparing the CA10 virus-like particles is as follows:

The cells are subjected to twice breaking by high-pressure homogenization at 1300 bar, and the resultant is subjected to deep filtration or centrifuging at 7000 rpm for 40 min to obtain a clarified liquid; the clarified liquid is subjected to ultrafiltration by using a buffer formed from 50 mM Tirs and 250 mM NaCl and 300 KD membrane package to obtain reflux. The reflux is subjected to ion exchange chromatography, and the eluate is collected to obtain a first-step chromatography protein solution; then the first-step chromatography protein solution is diluted with 500 mM PB to a PB concentration of 60 mM, and subjected to hydroxyapatite chromatography, eluting is performed using a 200 mM PB buffer, and the eluate is collected to obtain a second-step chromatography protein solution. After the two-step chromatography, the protein solution is purified by using a 10 to 50 mM PB buffer at a pH of 6.8 to 7.4 comprising 100 to 300 mM NaCl and 0.05%0 to 3%0 (w/v) Tween-80, and the eluate having an absorbance value at UV 280 nm is collected to obtain the target protein (VLP protein) purified solution.

In the fourth aspect, the present invention provides use of the CA10 virus-like particles prepared according to the above method in the preparation of a vaccine for hand-foot-and-mouth disease.

In the fifth aspect, the present invention provides a vaccine for hand-foot-and-mouth disease. The CA10 virus-like particles prepared according to the above method are subjected to adsorption with an aluminum hydroxide adjuvant to prepare a vaccine, which has a VLP protein content of 5 to 40 µg/ml, a content of the aluminum hydroxide adjuvant of 0.30 to 0.60 mg/ml, and a pH value of 6.0 to 7.4.

Preferably, each dose (0.5 ml) of a human vaccine contains:

| | |
|---|---|
| CA10 virus-like particles (calculated by protein) | 2.5 to 20 µg |
| Aluminum adjuvant (calculated by aluminum ion) | 0.15 to 0.30 mg |

The vaccine has good immunogenicity, safety, immune characteristics and biological activity, and will not cause retrovirus and potential RNA carcinogenic risks. The process is simple, does not use large-scale ultracentrifuge equipment, and is easier to realize large-scale preparation and purification.

With the above technical solutions, the present invention has at least the following advantages and beneficial effects:

(1) A high-efficiency expression strain can be easily obtained. In the present invention, the design of the P1 and 3CD protein gene sequences of CA10 is optimized, a recombinant expression vector for efficiently expressing the CA10 virus-like particles is constructed, and the high-efficiency expression of the virus-like particles (VLP or VLPs) is realized by the *Hansenula* expression system.

(2) The expression strain has good stability. The recombinant expression vector can undergo homologous recombination with the chromosomal genomic DNA of the yeast host cell, and the vector has good stability and is not easy to lose. The fermentation expression product is stored in peroxisomes to prevent degradation by proteases.

(3) The CA10 virus-like particles of the present invention are suitable for preparing vaccines. The protein of the present invention can be correctly processed, modified and folded in *Hansenula* without excessive glycosylation. After the fermented expression product is purified, the purified sample is observed by electron microscope to show virus-like particles, the particle diameter is about 30 nm, and the particles are complete and regular. The present invention provides CA10 virus-like particles without carrying viral nucleic acid, without potential carcinogenic risk, with good safety, immune characteristics and biological activity, which can be prepared and purified on a large scale, and can be used to prepare VLP vaccines with good economic value and application prospects.

(4) The present invention can obtain VLP samples with high purity and high yield through a well-designed purification process. In the present invention, the recombinantly expressed engineering fungi are cultured by high-density fermentation and induced by methanol to express CA10 virus-like particle proteins. The fungi are collected by centrifugation, and subjected to breaking by high-pressure homogenization. The supernatant is subjected to purification such as ultrafiltration, ion exchange chromatography, hydroxyapatite chromatography and molecular sieve chromatography to obtain the CA10 virus-like particles. The method of the present invention adopts ultrafiltration and three-step chromatography with simple operation, strong process controllability and high antigen recovery rate, does not use large ultracentrifuge equipment, and is easier to realize large-scale preparation and purification.

SPECIFIC MODES FOR CARRYING OUT THE EMBODIMENTS

The present invention provides a method for preparing and purifying CA10 virus-like particles, and use thereof in the field of vaccines. The recombinantly expressed *Hansenula* engineering fungi were cultured by high-density fermentation and induced by methanol to express CA10 virus-like particle proteins. The fungi were collected by centrifugation and subjected to breaking by high-pressure homogenization. The supernatant was subjected to purification such as ultrafiltration, ion exchange chromatography, hydroxyapatite chromatography and molecular sieve chromatography to obtain the CA10 virus-like particles. The CA10 virus-like particles provided by the present invention and the vaccine prepared therefrom have good immunogenicity, safety, immune characteristics and biological activity, and simple process. The purification adopts chromatography methods, which are more favorable to linear amplification compared with density gradient centrifugation, and a large-scale preparation and purification can be performed to obtain a high-purity (greater than 99%) VLP protein stock solution, which can be used to prepare a vaccine for preventing CA10 infection, with good economic value and application prospects.

The present invention first provides a high-efficiency strain expressing A10 virus-like particles obtained from *Hansenula* expression system, comprising the following steps:
(1) Gene sequence optimization and synthesis: The sequence of the yeast secretion signal peptide or the sequence of the transcription termination signal recognized by yeast is deleted from the nucleotide sequence encoding the P1 and 3CD proteins of CA10 virus. The preferred codon of *Hansenula* was used for sequence optimization and synthesis. The optimized nucleotide sequences of the P1 and 3CD genes of the CA10 virus are represented by SEQ ID NOs: 1 and 2, respectively.

(2) Construction of recombinant expression vector: The optimized synthesized P1 and 3CD genes were subjected to double enzyme digestion with EcoRI and BamHI, and respectively constructing with a vector PMV-05 (refer to ZL201210592813.5 for the construction method of the vector PMV-05) having been double-enzyme digested by EcoRI/BamHI to obtain a PMV-05-P1 recombinant expression vector and a PMV-05-3CD recombinant expression vector, and then the PMV-05-P1 recombinant expression vector and the PMV-05-3CD recombinant expression vector were subjected to enzyme digestion with SacI/XhoI and SacI/SalI, respectively, and constructing to obtain a PMV-05-P1-3CD co-expression vector.

(3) Obtaining a CA10 recombinant *Hansenula* engineering strain: The recombinant co-expression vector PMV-05-P1-3CD was transformed into *Hansenula* ATCC26012 uracil auxotroph host cell AU-0501 by electroporation (see ZL201210592813.5 for the strain, with an accession number of CGMCC No. 7013), and a CA10 recombinant *Hansenula* engineering strain was obtained by stabilizing culturing and screening.

The present invention also provides a purification method of CA10 virus-like particles expressed from the *Hansenula* expression system, which is more favorable to linear amplification, can realize large-scale preparation and purification, and can obtain a high-purity (greater than 99%) VLP protein (a virus-like particle vaccine) stock solution, which can be used to prepare a vaccine for preventing CA10 infection, with good economic value and application prospects.

The method for preparing the CA10 virus-like particles comprises the following steps:

(1) subjecting the recombinant *Hansenula* engineering fungi containing CA10 coat protein P1 gene and 3CD protease gene to fermentation;

(2) breaking the engineering fungi, clarifying the target product and performing ultrafiltration;
(3) ion exchange chromatography;
(4) hydroxyapatite chromatography; and
(5) molecular sieve chromatography.

The above method can be used to obtain a high-purity (greater than 99%) VLP stock solution for preparing a human vaccine. The present invention adopts three-step chromatography, the process is simple, the antigen recovery rate is up to 40% or more, the production process is highly controllable, and can realize large-scale production, with high social value and economic value.

The following examples are used to illustrate the present invention, but not to limit the scope of the present invention. Unless otherwise specified, the examples are in accordance with conventional experimental conditions, such as conditions suggested by Sambrook J & Russell DW (Molecular Cloning: a Laboratory Manual, 2001), or conditions suggested by the manufacturer's instructions.

The percentage "%" involved in the present invention refers to mass percentage unless otherwise specified; however, the percentage of a solution, unless otherwise specified, refers to the number of grams of solute contained in 100 mL of the solution. "% o" refers to the number of grams of solute contained in 1000 mL of the solution.

Example 1: Obtaining of CA10 Recombinant Hansenula Engineering Fungi

According to the nucleotide sequences of the P1 and 3CD proteins of the recently prevalent Coxsackie virus A10 strain, the Vector software was used to optimize the design of the P1 and 3CD gene sequences according to preferred codons of Hansenula to increase the expression level thereof.

In the optimization process, the sequence of the yeast secretion signal peptide or the sequence of the transcription termination signal recognized by the yeast was deleted. In order to prevent an excessively high GC content of the translated mRNA and the secondary structure of the mRNA from affecting the translation efficiency, and considering the sites of enzyme digestion, the gene sequence at certain positions was adjusted appropriately while ensuring that the amino acid remained unchanged. The optimized nucleotide sequences of the P1 and 3CD genes of the CA10 virus are represented by SEQ ID NOs: 1 and 2, respectively.

The present invention uses the expression vector PMV-05 to construct the CA10 recombinant expression vector. Specifically, the optimized synthesized P1 and 3CD genes were subjected to double enzyme digestion with EcoRI and BamHI, and respectively constructing with the expression vector PMV-05 having been double-enzyme digested by EcoRI/BamHI to obtain a PMV-05-P1 recombinant expression vector and a PMV-05-3CD recombinant expression vector, and then the PMV-05-P1 recombinant expression vector and the PMV-05-3CD recombinant expression vector were subjected to enzyme digestion with SacI/XhoI and SacI/SalI, respectively, and constructing to obtain a PMV-05-P1-3CD co-expression vector.

The present invention uses the patented Hansenula uracil auxotroph host strain AU-0501 to screen the CA10 recombinant Hansenula engineering strain, specifically the recombinant co-expression vector PMV-05-P1-3CD was transformed into Hansenula ATCC26012 uracil auxotroph host cell AU-0501 by electroporation, and a CA10 recombinant Hansenula engineering strain was obtained by stabilizing culturing and screening by methods such as PCR, SDS-PAGE and WB.

Figure 1:
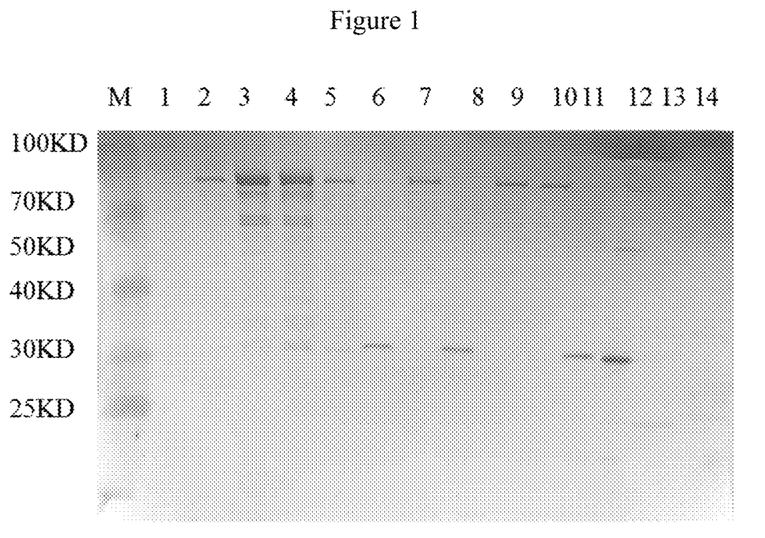
FIG. 1 shows the Western blot detection result of inducibly expressed protein of some strains screened from the recombinant *Hansenula* engineering strain in Example 1 of the present invention.

The Western blot detection result of induced expression of some strains screened from the CA10 recombinant Hansenula engineering strain is shown in FIG. 1. In FIG. 1, 1: negative control; 2-5: PMV-05-P1 transformed strain; 6-14: PMV-05-P1-3CD transformed strain. It should be noted that 3CD is a protease that can cleave P1 protein to assemble into VLP, and the 3CD protease is removed in subsequent purification. Not the P1 protein in all transformants can be efficiently cleaved by 3CD protease and assembled into VLP.

The Western blot result shows that: the expression product of the PMV-05-P1-3CD transformed strain can specifically bind to the monoclonal antibody, and there is a relatively obvious reaction band at 33 KD, indicating that a CA10 recombinant Hansenula expression strain (a Hansenula engineering strain that efficiently expresses CA10 virus-like particles) is obtained by screening.

An engineering strain—Hansenula polymorpha CA10-W that can stably express the target protein at the highest protein expression level was selected therefrom, and sent to the China General Microbiological Culture Collection Center for depositing, the accession number is CGMCC No. 19850, and the depositing date is May 20, 2020.

Example 2: Cultivation of the Recombinant CA10 Yeast Expression Strain by Fermentation in a 30 L Fermenter The strain CA10-W was inoculated into 100 ml of a primary seed culture medium (0.67% yeast nitrogen-source medium, 0.5% ammonium sulfate, and 2% glucose), and cultured in a shaker at 33° C. and 200 rpm for 18 to 22 h. The primary seed culture solution was taken and inoculated into 1000 ml of a secondary seed culture medium, and cultivation was performed in a shaker at 33° C. and 200 rpm for 21 to 23 h. The secondary seed culture solution was inoculated into a 30 L fermenter, the pH value of the fermentation broth was adjusted by ammonia water to maintain at 5.0±0.5, the fermentation temperature was 30±1° C., the rotating speed was controlled at 350 to 750 rpm, and the air flow rate was 0.5 to 1.0 $m^3$/h. High-density fermentation requires supplementation of pure oxygen. Dissolved oxygen was controlled at 20% to 60%. The carbon source in the fermentation medium was exhausted at 16 h to 18 h. A total of glycerol added was 2.0 L, and the total growth period of fungi was about 26 h to 28 h. The weight of wet fungi can reach about 0.3 to 0.4 g/ml. Derepression stage: the stirring speed was set to 750 rpm, the air flow rate was 1.0 $m^3$/h, the dissolved oxygen was controlled at 20% to 60%, and 1 L of a derepressor solution (the derepressor solution was a mixture of methanol and glycerol, and the volume ratio of glycerol to methanol was 1:4) was added for derepression culturing at 36 h to 41 h (totally 11 h to 13 h) during fermentation. Induction stage: methanol induction was performed at 41 h to 86 h (40 h to 44 h) during fermentation, dissolved oxygen was maintained at about 20% to 40%. The end of fermentation: at 82 h to 86 h, when methanol was consumed completely, the dissolved oxygen rose to 80% or more, the fermentation was finished to discharge after the temperature was lowered to 2° C. to 8° C., and the weight of wet fungi was maintained at 0.26 to 0.30 g/ml.

Identification of CA10 virus-like particles expressed by Hansenula: The samples were taken at different time (0 h, 4 h, 8 h, 12 h, 16 h, 20 h, 24 h, 28 h, 32 h, 36 h, 40 h, 44 h) after the above induction for protein western blot detection by using rabbit anti-CA10-VP1 polyclonal antibody (the preparation method of the polyclonal antibody was as follows: after purification of CA10-VP1 protein expressed by E. coli, a Freund's adjuvant was added, a rabbit was immunized with the above CA10-VP1 protein for four times, the serum was separated, and purification was performed using Protein A to obtain the polyclonal antibody) as the primary antibody, HRP-goat anti-rabbit-IgG (Sigma company) as the secondary antibody, and DAB color development. The results were shown in FIG. 2.

Figure 2:
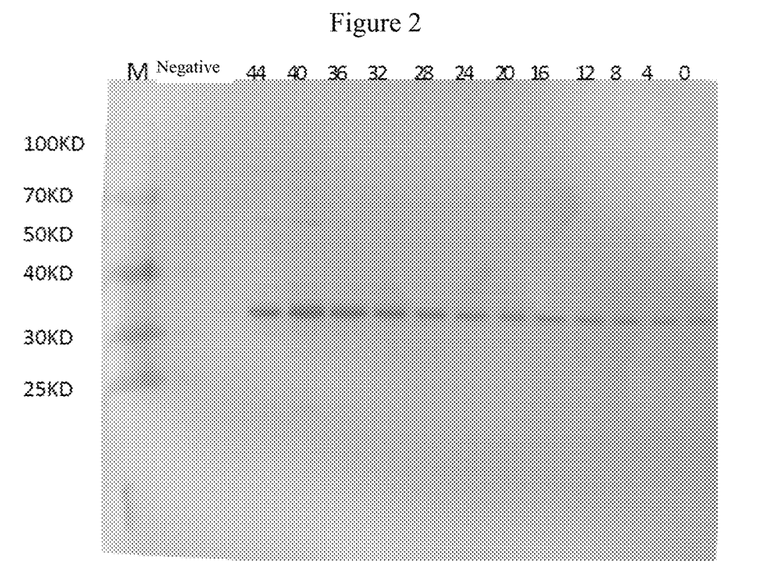
FIG. 2 shows the Western blot detection result of protein in samples of the engineering fungi CA10-W at different time (0, 4, 8, 12, 16, 20, 24, 28, 32, 36, 40, and 44 h) after induction in Example 2 of the present invention. M is a low molecular weight protein standard (Beijing Quanshijin Biotechnology Co., Ltd.).

Western blot results show that: the expression product can specifically bind to the monoclonal antibody, and there is a relatively obvious reaction band at 33 KD, indicating that the foreign protein can be expressed well in yeast cells.

Determination of the expression level of recombinant CA10 virus-like particles by fermentation: The rabbit polyclonal antibody was 1000-fold diluted, and 100 μl was added to a 96-well ELISA plate, to be coated overnight at 4° C. The coating solution was removed completely, and a washing solution PBST was filled to wash the ELISA plate. A blocking solution (1% BSA in PBST solution) was filled in the ELISA plate to incubate at 37° C. for 2 h. The supernatant collected by centrifugation after breaking and the reference sample were diluted in gradient series. After the blocking solution was completely removed, 100 μl of the sample to be tested and the reference sample (the initial concentration of the reference sample was 100 ng/ml) were added to each well to incubate at 37° C. for 1 h. A washing solution PBST was filled to wash the ELISA plate for 3 times. 100 μl of a HRP-labeled mouse monoclonal antibody (1:5000 diluted) was added to each well to incubate at 37° C. for 1 h. The enzyme-labeled solution was completely removed, and a washing solution PBST was filled to wash the ELISA plate for 3 times. 100 μl of a TMB color developing solution was added to each well to keep in the dark at 37° C. for 15 min. 50 μl of 2 mol/L $H_2SO_4$ was added to each well to terminate. The $OD_{450\,nm}$ value was measured with a microplate reader, and the antigen content was calculated by the double parallel line method. The measurement results were shown in Table 1.

500 mM NaCl, 2 mM PMSF, 0.05% Tween-80, pH 8.0), and a high-pressure homogenizer was used to break the cells twice under the pressure of 1300 bar, and the cell breakage rate was up to 85% or more.

Clarification: The cell-broken liquid was subjected to depth filtration, the filter membrane package was washed with a washing solution (50 mM Tris, 2 mM EDTA-Na2, 500 mM NaCl, 0.05% Tween-80, pH 8.0), the filtration flow rate was 1200 ml/min/m², and the clarified liquid was collected.

Ultrafiltration: The collected clarified liquid was subjected to ultrafiltration by a 300 KD membrane package using 50 mM Tris+250 mM NaCl+5% glycerol (pH 8.0) to remove small molecular substances, and the ultrafiltrate was collected to obtain a crude pure product.

Ion exchange chromatography: with the Capto Q chromatography medium as an example, a buffer of 5 to 10 column volumes comprising 50 mM Tris+250 mM NaCl+5% glycerol (pH 8.0) was used to perform equilibrium, then the sample was loaded, the eluate (i.e., a first-step chromatography protein solution) having an ultraviolet absorption peak at UV 280 nm was collected, and 1 mol/L NaOH was used to regenerate the chromatography medium.

Hydroxyapatite chromatography: a 500 mM PB solution was added to the first-step chromatography protein solution to have a final concentration of 60 mmol/L PB, a buffer of 5 column volumes comprising 60 mM PBS+5% glycerol solution (pH 8.0) was used to perform equilibrium, then the sample was loaded, equilibrium was performed with another 2 column volumes, 200 mM PBS+5% glycerol solution (pH 8.0) were used for eluting, and the eluate (i.e., a second-step chromatography protein solution) having an ultraviolet absorption peak at UV 280 nm was collected.

Molecular sieve chromatography: a Sephacryl S-300HR packing material was used, 20 mM PB (pH6.8) and 150 mM NaCl solution and 0.1%0 Tween-80 buffer were used to purify the second-step chromatography protein solution, and the target protein having an ultraviolet absorption peak at UV 280 nm was collected. The purity of the protein solution was determined to be 100% by HPLC. The detection results were shown in FIG. 3. The VLP has a peak corresponding

TABLE 1

Test results of antigen content of cell-broken fermentation broth (ELISA method)

| | Dilution folds of the reference sample | | | | |
|---|---|---|---|---|---|
| | Standard 1 20 | Standard 2 40 | Standard 3 80 | Standard 4 160 | Standard 5 320 |
| $OD_{450\,nm}$ average value | 1.756 | 0.999 | 0.561 | 0.284 | 0.116 |
| Sample dilution | 1500 | 3000 | 6000 | 12000 | 24000 |
| Sample $OD_{450\,nm}$ average value | 1.187 | 0.672 | 0.422 | 0.218 | 0.117 |
| Antigen content of cell-broken fermentation broth (μg/ml) | | | 225 | | |

ELISA measurement results show that the antigen content of CA10 virus-like particles in the cell-broken fermentation broth is 225 μg/ml. The CA10 virus-like particles expressed by Hansenula cells have a relatively high expression level.

Example 3: Separation and Purification of CA10 Virus-Like Particles

Cell collection: The fermentation broth of strain CA10-W was collected, centrifugation was performed at 6500 rpm to collect precipitates, and a cell washing buffer was used to wash the cells twice.

Figure 3:
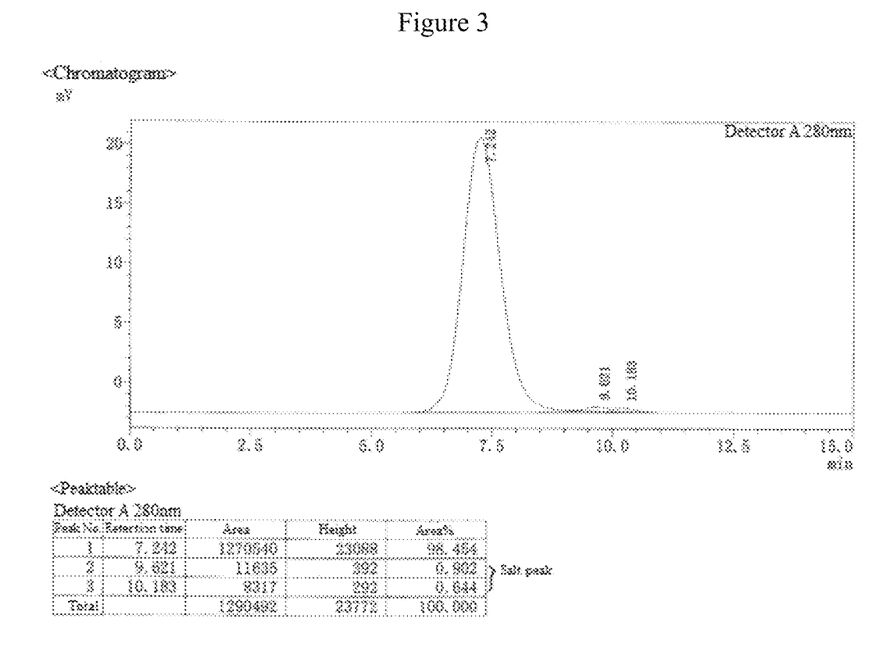
FIG. 3 shows the HPLC purity detection result in Example 3 of the present invention.

Breaking: The collected Hansenula cells were resuspended in a cell lysis buffer (50 mM Tris, 2 mM EDTA-Na2, to the retention time of 7.242 min, and the peaks corresponding to the retention time of 9.621 min and 10.183 min are solvent peaks.

Detection of the target protein concentration (Lowry method): 0 ml, 0.2 ml, 0.4 ml, 0.6 ml, 0.8 ml, and 1.0 ml of a standard protein bovine serum albumin solution (200 μg/ml) were accurately measured, and added in test tubes, respectively, distilled water was added to supplement to 1 ml, and meanwhile, 1 ml of the 2-fold diluted purified protein solution was measured to add in a test tube, 5 ml of an alkaline copper solution and 0.5 ml of a phenol reagent were added, respectively, and in a cuvette, the absorbance value at the wavelength of 650 nm was measured. A standard curve was drawn with the protein content of the standard protein as the abscissa and the absorbance value as the ordinate, and the concentration of the protein solution to be tested was calculated. The test results were shown in Table 2.

TABLE 2

Test results of purified protein concentration (Lowry method)

| | Standard concentration μg/ml | | | | | |
|---|---|---|---|---|---|---|
| | Standard 1 0 | Standard 2 40 | Standard 3 80 | Standard 4 120 | Standard 5 160 | Standard 6 200 |
| OD650 nm | 0.000 | 0.140 | 0.270 | 0.391 | 0.506 | 0.622 |
| Sample OD650 nm | 0.253 | 0.247 | OD650 nm average value | | | 0.250 |
| Calculated concentration μg/ml | 78.8 | | Dilution folds 4 | | Final concentration of purified protein solution μg/ml | 315.2 |

The test results of Lowry method show that the final concentration of the purified protein is 315.2 μg/ml.

Figure 4:
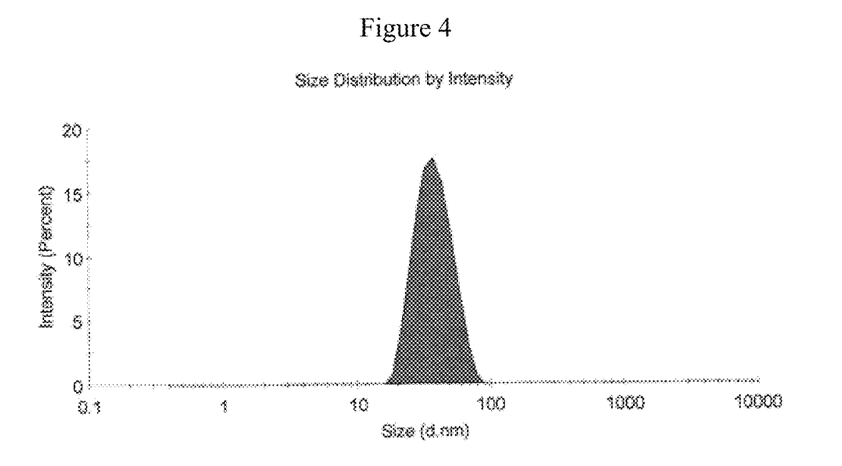
FIG. 4 shows a dynamic light scattering spectrum of the purified CA10 virus-like particles in Example 3 of the present invention.

Dynamic light scattering analysis of the target protein solution: an appropriate amount of the purified CA10 protein solution was taken and added into a sample pool, the temperature was set to 25° C., the equilibrating time was 90 s, the number of automatic cycles was set, the measurement was started, and the results were analyzed. The results show that the recombinant CA10 virus-like particles are intact, with a particle diameter of more than 99% in the distribution of 24 nm to 30 nm, the PDI was 0.08, and the dynamic light scattering spectrum is shown in FIG. 4.

Figure 5:
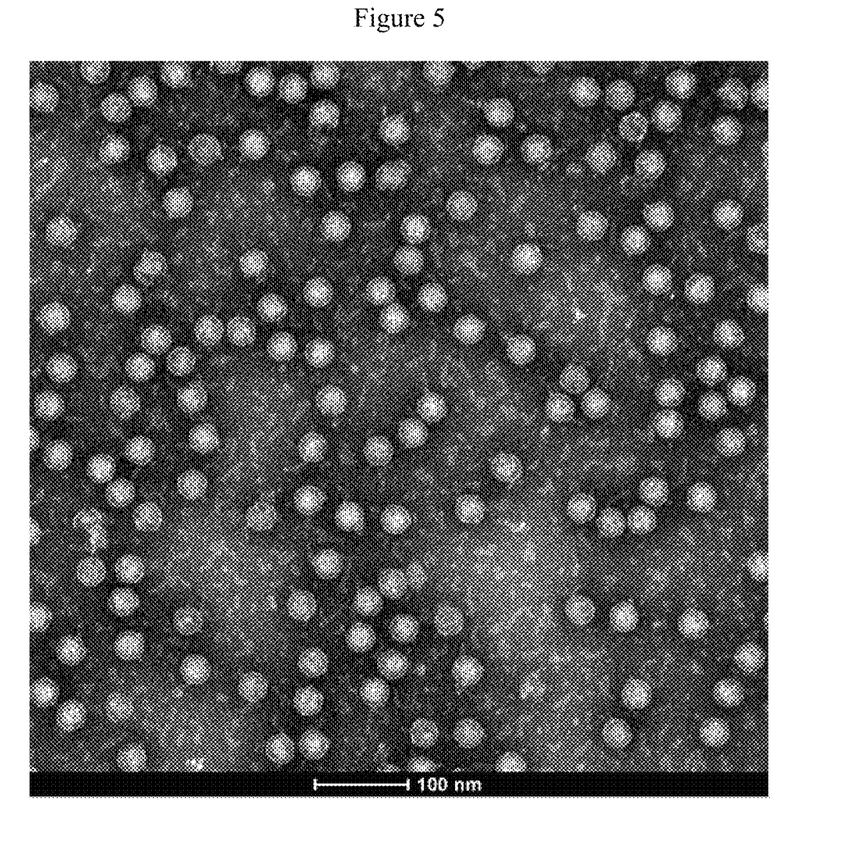
FIG. 5 shows a transmission electron micrograph of the purified CA10 virus-like particles in Example 3 of the present invention (magnification: 120000).

Electron microscopy analysis of the target protein solution: an appropriate amount of purified CA10 protein solution was taken, dropped on a copper mesh, and stored in the dark for 5 min, excessive liquid was removed, 1% phosphotungstic acid was used for staining for 2 min, and the CA10 VLPs were analyzed by a transmission electron microscope (TEM). The results show that the CA10 protein is in form of a virus-like particle, with the icosahedral structure of a natural virus, the diameter of the virus particle is about 30 nm, and the particles are intact and regular (FIG. 5).

Determination of the antigen content of the target protein solution (double antibody sandwich ELISA): the rabbit polyclonal antibody was 1000-fold diluted, 100 μl of the sample was taken and added into a 96-well ELISA plate, to be coated overnight at 4° C. The coating solution was removed completely, and a washing solution PBST was filled to wash the ELISA plate. A blocking solution (1% BSA in PBST solution) was filled in the ELISA plate to incubate at 37° C. for 2 h. The blocking solution was removed completely, 100 μl of the sample to be tested and the reference sample (the initial concentration was 100 ng/ml) were added to each well to incubate at 37° C. for 1 h. A washing solution PBST was filled to wash the ELISA plate for 3 times. 100 μl of a HRP-labeled mouse monoclonal antibody (1:5000 diluted) was added to each well to incubate at 37° C. for 1 h. The enzyme-labeled solution was completely removed, and a washing solution PBST was filled to wash the ELISA plate for 3 times. 100 μl of a TMB color developing solution was added to each well to keep in the dark at 37° C. for 15 min. 50 μl of 2 mol/L $H_2SO_4$ was added to each well to terminate. The OD450 nm value was measured with a microplate reader, and the antigen content was calculated by the double parallel line method. The test results of double antibody sandwich ELISA were shown in Table 3.

TABLE 3

Test results of double antibody sandwich ELISA

| | Dilution folds of the reference sample | | | | |
|---|---|---|---|---|---|
| | Standard 1 20 | Standard 2 40 | Standard 3 80 | Standard 4 160 | Standard 5 320 |
| $OD_{450\ nm}$ average value | 1.186 | 0.672 | 0.422 | 0.218 | 0.117 |
| Dilution folds of the sample | 500 | 1000 | 2000 | 4000 | 8000 |
| $OD_{450\ nm}$ average value of the sample | 1.137 | 0.860 | 0.471 | 0.234 | 0.121 |
| Antigen content of the purified protein solution (μg/ml) | | | 310.4 | | |

Example 4: Preparation of a Recombinant CA10 Virus-Like Particle Vaccine

Main index control: the content of antigen (CA10 virus-like particles) was 20 μg/ml; the content of aluminum was controlled at 0.40 to 0.60 mg/ml; and the pH value was controlled at 6.6 to 7.4.

Preparation method: The homemade aluminum hydroxide adjuvant was diluted to 0.50 mg/ml with a sterile 0.9% sodium chloride solution. The purified CA10 stock solution was slowly added dropwise to the adjuvant to make it fully adsorbed, and the vaccine preparation was completed. The test standards and test results of the prepared vaccine were shown in Table 4.

TABLE 4

Test results of the recombinant CA10 virus-like particle vaccine

| Test items | Quality standard | Test results |
|---|---|---|
| Antigen content | Not less than 16.0 µg/ml | 20.1 µg/ml |
| Aluminum content | 0.40 to 0.60 mg/ml | 0.49 mg/ml |
| pH value | 6.0 to 8.0 | 6.8 |
| Adsorption rate | >95.0% | 99.4% |
| Osmolality | 300 ± 65 mOsmol/kg | 293 mOsmol/kg |
| Fungal endotoxin | Less than 5 EU/ml | In compliance with the regulation |

The results in Table 4 show that the test indicators of the recombinant CA10 virus-like particle vaccine all meet the test standards.

Example 5: Immunogenicity ($ED_{50}$) Test of the Recombinant CA10 Virus-Like Particle Vaccine Test vaccine: The recombinant CA10 virus particle vaccine containing aluminum hydroxide adjuvant prepared in Example 3.

Experimental animals: 50 SPF-grade NIH mice of 18 to 22 g were selected and purchased from China Food and Drug Research Institute.

Animal immunization: 10 mice were injected with proportionally diluted vaccines of 2 µg/0.5 ml, 0.5 µg/0.5 ml, 0.125 µg/0.5 ml, and 0.03125 µg/0.5 ml and aluminum hydroxide adjuvant, respectively, each with 0.5 ml intraperitoneal injection, and 28 days after immunization, eyeballs were taken and blood was collected. The collected blood was kept at 37° C. for 1 h and 4° C. for 3 to 4 h, centrifugation was performed at 4000 rpm for 10 min, and the supernatant was pipetted for detection.

Neutralizing antibody detection: The serum sample was diluted with MEM culture solution of 2% newborn calf serum at a ratio of 1:8, and inactivation was performed in a water bath at 56° C. for 30 min. A 96-well cell culture plate was used, and 50 µl of a diluting solution was added to each well. The corresponding sample of 50 µl was added to each well, after being mixed well, a multichannel pipette was used to suck 50 µl from row A to row B to mix well, mixing and diluting were performed in sequence till row D, and 50 µl was discarded. The CA10 virus attack strain was serially diluted to 100 $CCID_{50}$/0.05 ml, 50 µl was taken and dropped vertically into each well, the cell culture plate was tapped gently to mix well, and neutralizing was performed at 37° C. for 2 h. The RD cells (the cells were resuscitated and expanded in advance) were digested with a digestive solution to prepare a cell suspension with a concentration of $2 \times 10^5$ cells/ml, 0.1 ml of the cell suspension was added to each well (including the virus back titration well) to mix well, and incubation and culture was performed in a $CO_2$ incubator at 35° C. An inverted microscope was used to observe the CPE every day, and the virus titration results were recorded, with the reciprocal of the highest dilution of serum to inhibit 50% cytopathy as the endpoint titer. The final result was determined within 6 to 7 days. According to the test results, the antibody positive conversion rate was shown in Table 5.

TABLE 5

Calculation results of the antibody positive conversion rate

| Dilution | Protein content | Mouse antibody Positive | Mouse antibody Negative | Positive conversion rate | Cumulative total Positive | Cumulative total Negative | Positive conversion rate |
|---|---|---|---|---|---|---|---|
| 1:5 | 2 µg/0.5 ml | 10 | 0 | 100% | 19 | 0 | 100% |
| 1:20 | 0.5 µg/0.5 ml | 7 | 3 | 50% | 9 | 3 | 75% |
| 1:80 | 0.125 µg/0.5 ml | 2 | 8 | 10% | 2 | 11 | 15% |
| 1:320 | 0.03125 µg/0.5 ml | 0 | 10 | 0% | 0 | 21 | 0% |

Calculation according to Reed-Muench method: $ED_{50} = 0.28$ (µg)

According to the results of the mouse $ED_{50}$ experiment, the CA10 virus-like particle vaccine prepared by the present invention can make the antibody positive conversion rate reach 50% after immunizing the mice with only 0.28 µg. Therefore, the CA10 virus-like particle of the present invention has strong immunogenicity.

Example 6: Abnormal Toxicity Test of the Recombinant CA10 Virus-Like Particle Vaccine Vaccine sample: the recombinant CA10 virus-like particle vaccine prepared in Example 3.

Experimental animals: 10 SPF-grade KM mice of 18 to 22 g, and 4 SPF-grade Hartley guinea pigs of 250 to 350 g, all purchased from Beijing Weitong Lihua Experimental Animal Technology Co., Ltd.

Experimental method: The weight of each experimental animal was weighed before injection, the mouse was 18 to 22 g, and the guinea pig was 250 to 350 g. The vaccine was injected into 5 mice and 2 guinea pigs, the mice were intraperitoneally injected with 0.5 ml/mouse, the guinea pigs were intraperitoneally injected with 5.0 ml/guinea pig, and observation was performed for 7 days. At the same time, a blank control of the same batch of animals was set up. Qualification criteria: During the observation period, the animals in the blank control and the experimental groups survived without abnormal reaction, and each animal gained weight in due time. The animal test results were shown in Table 6.

TABLE 6

Animal experiment results

| Animal species | Number | Initial weight (g) | Final weight (g) |
|---|---|---|---|
| Mouse experimental group | 1 | 20.2 | 29.8 |
|  | 2 | 19.3 | 28.7 |
|  | 3 | 20.0 | 31.0 |
|  | 4 | 21.0 | 30.2 |
|  | 5 | 21.2 | 29.9 |
| Mouse control group | 1 | 19.5 | 31.3 |
|  | 2 | 21.4 | 32.2 |
|  | 3 | 21.0 | 29.6 |
|  | 4 | 20.5 | 28.7 |
|  | 5 | 21.5 | 30.4 |
| Guinea pig experimental group | 1 | 300.2 | 412.3 |
|  | 2 | 322.2 | 412.9 |
| Guinea pig control group | 1 | 286.5 | 389.6 |
|  | 2 | 310.2 | 401.3 |

The results show that the animals in the blank control and experimental groups survived during the observation period without abnormal reaction, and the weight of each animal increased on the 8th day. It is proved that the recombinant CA10 virus-like particle vaccine has no abnormal toxicity and good safety to the experimental animals.

Example 7: Study on the Immune Serum Protective Effect of the CA10 Virus-Like Particle Vaccine Test serum: immune serum obtained from the mice immunized with the CA10 virus-like particle vaccine prepared in Example 3.

Experimental animals: 5 litters of 1-day-old Blab/c suckling mice, SPF grade, purchased from China Institute for Food and Drug Control.

Experimental method: 50 µl of virus (CA10 virus, strain source: FZ-2014 KY012321, virus titer: 8.5 lgCCID$_{50}$/ml) was used for intraperitoneally attacking, respectively, and within 1 hour each litter of suckling mice were simultaneously immunized intraperitoneally with 50 µl immune serum having neutralizing antibody titers of 341.33U, 56.89U, 9.48U, and 1.58U obtained from mice immunized with the CA10 virus-like particle vaccine and negative control (virus culture solution), respectively. The morbidity and mortality of the suckling mice were recorded every day for 21 consecutive days, and the morbidity and mortality of the suckling mice in each group were counted at the end of the observation period.

Figure 6:
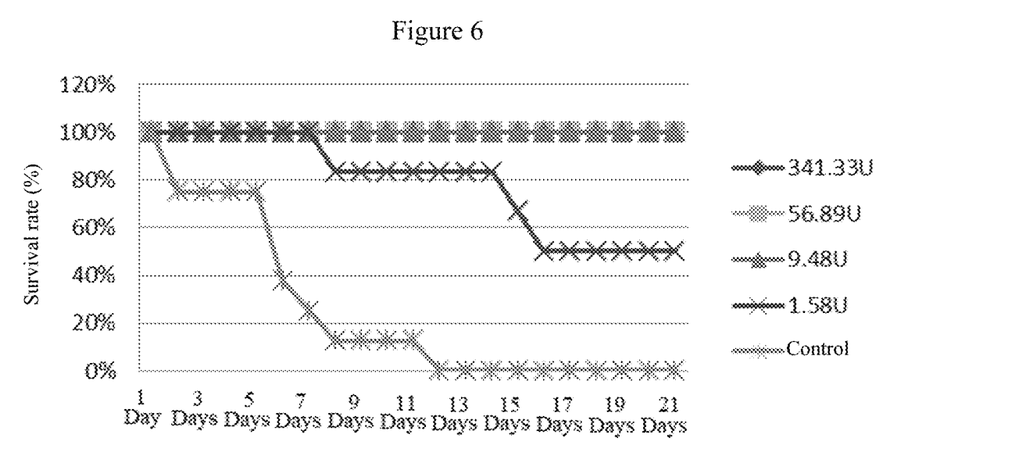
FIG. 6 shows the protection effect of immune serum of the CA10 virus-like particle vaccine in Example 7 of the present invention.

The test results were shown in FIG. 6. The suckling mice in the control group all died and the test was successful. The vaccine groups all show different protective effects. According to the immune serum titers of 341.33U, 56.89U, 9.48U, and 1.58U, the protection rates of the recombinant CA10 virus-like particle vaccine were 100%, 100%, 100%, and 50%, respectively. According to the Reed-Muench method, the average half animal protection neutralizing antibody titer (ED$_{50}$) was calculated to be less than 1.58U. The recombinant CA10 virus-like particle vaccine has a good immune protection effect in 1-day-old suckling mice.

Although the present invention has been described in detail above with general descriptions and specific embodiments, some modifications or improvements can be made on the basis of the present invention, which is obvious to a person skilled in the art. Therefore, these modifications or improvements made without departing from the spirit of the present invention belong to the scope of the present invention.

INDUSTRIAL APPLICABILITY

The present invention provides a *Hansenula* engineering fungus that efficiently expresses CA10 virus-like particles and use thereof. The engineering fungus comprises a recombinant vector carrying P1 and 3CD genes of the CA10 virus, and the starting strain of the engineering fungus is uracil auxotroph *Hansenula* AU-0501. P1 and 3CD genes are optimized according to preferred codons of *Hansenula*. The present invention also provides a preparation method of CA10 virus-like particles, comprising: culturing engineering fungi, expressing CA10 virus-like particles, and separating and purifying virus-like particles by ultrafiltration and three-step chromatography. The CA10 virus-like particles provided by the present invention and the vaccine prepared therefrom have good immunogenicity, safety and biological activity, the process is simple, the chromatography method is adopted for purification, and large-scale preparation and purification can be realized to obtain a VLP protein stock solution with high purity (greater than 99%), which can be used to prepare a vaccine to prevent CA10 infection, with good economic value and application prospects.

What is claimed is:

1. An engineered *Hansenula* cell comprising a PMV-05 vector comprising a nucleic acid molecule having a nucleotide sequence of a P1 gene of Coxsackievirus A10 (CA10) and a nucleotide sequence of a 3CD gene of CA10, wherein:
   the nucleotide sequence of the P1 gene has the nucleotide sequence set forth in SEQ ID NO: 1; and
   the nucleotide sequence of the 3CD gene has the nucleotide sequence set forth in SEQ ID NO:2.

2. The engineered *Hansenula* cell according to claim 1, wherein the engineered *Hansenula* cell comprises a *Hansenula polymorpha* CA10-W cell having China General Microbiological Culture Collection accession number 19850.

3. A process for preparing a purified Coxsackievirus A10 (CA10) virus-like particle comprising:
   culturing the engineered *Hansenula* cell according to claim 1 so as to express in the culture at least one 3CD protein and a plurality of P1 proteins;
   allowing the at least one 3CD protein to cleave the plurality of P1 proteins, thereby allowing self-assembly of the plurality of cleaved P1 proteins into a virus-like particle; and
   purifying the virus-like particle.

4. The process according to claim 3, further comprising adsorbing the purified virus-like particle onto an aluminum hydroxide adjuvant.

5. A vaccine for hand-foot-and-mouth disease comprising the virus-like particle according to claim 4, wherein the concentration of the virus-like particle is 5 to 40 μg/mL.

* * * * *